United States Patent [19]

Hascoet et al.

[11] Patent Number: 5,235,981
[45] Date of Patent: Aug. 17, 1993

[54] USE OF ULTRASOUND FOR DETECTING AND LOCATING A BONY REGION, METHOD AND APPARATUS FOR DETECTING AND LOCATING SUCH A BONY REGION BY ULTRASOUND

[75] Inventors: Gérard Hascoet, Paris; Francois Lacoste, Lyons; Emmanuel Blanc, St-Genis-Laval, all of France

[73] Assignee: Technomed International, Paris, France

[21] Appl. No.: 675,210

[22] Filed: Mar. 26, 1991

[30] Foreign Application Priority Data

Mar. 27, 1990 [FR] France .................. 90 03916

[51] Int. Cl.$^5$ .................. A61B 8/00; A61N 1/00
[52] U.S. Cl. .................. 128/660.01; 128/660.03; 128/24 AA
[58] Field of Search .................. 128/660.01, 660.06, 128/660.07, 661.03, 660.03, 24 A

[56] References Cited

U.S. PATENT DOCUMENTS

| | | | |
|---|---|---|---|
| 4,421,119 | 12/1983 | Pratt, Jr. | 128/660.01 |
| 4,754,763 | 7/1988 | Doemland | 128/739 |
| 4,905,671 | 3/1990 | Senge et al. | 128/24 AA |
| 4,979,501 | 12/1990 | Valchanor et al. | 128/24 AA |
| 5,079,951 | 1/1992 | Raymond et al. | 128/660.07 |

FOREIGN PATENT DOCUMENTS

| | | |
|---|---|---|
| 0324711 | 1/1989 | European Pat. Off. . |
| 0324163 | 7/1989 | European Pat. Off. . |
| 2318420 | 2/1977 | France . |
| 8809190 | 12/1988 | PCT Int'l Appl. . |
| 9001296 | 2/1990 | PCT Int'l Appl. . |
| 9001903 | 3/1990 | PCT Int'l Appl. . |

OTHER PUBLICATIONS

Copy of French Search Report.

*Primary Examiner*—Francis Jaworski
*Attorney, Agent, or Firm*—Cohen, Pontani, Lieberman, Pavane

[57] ABSTRACT

The invention relates to a method and to apparatus for detecting and locating a bony region by ultrasound. The apparatus comprises at least one ultrasound transducer component mounted on means for displacing it in three dimensions, which transducer emits signals that are received by processor means for determining the coordinates of a bony region and for storing said coordinates. The invention simplifies the procedure of detecting and locating the bony region and avoids the use of X-rays.

16 Claims, 4 Drawing Sheets

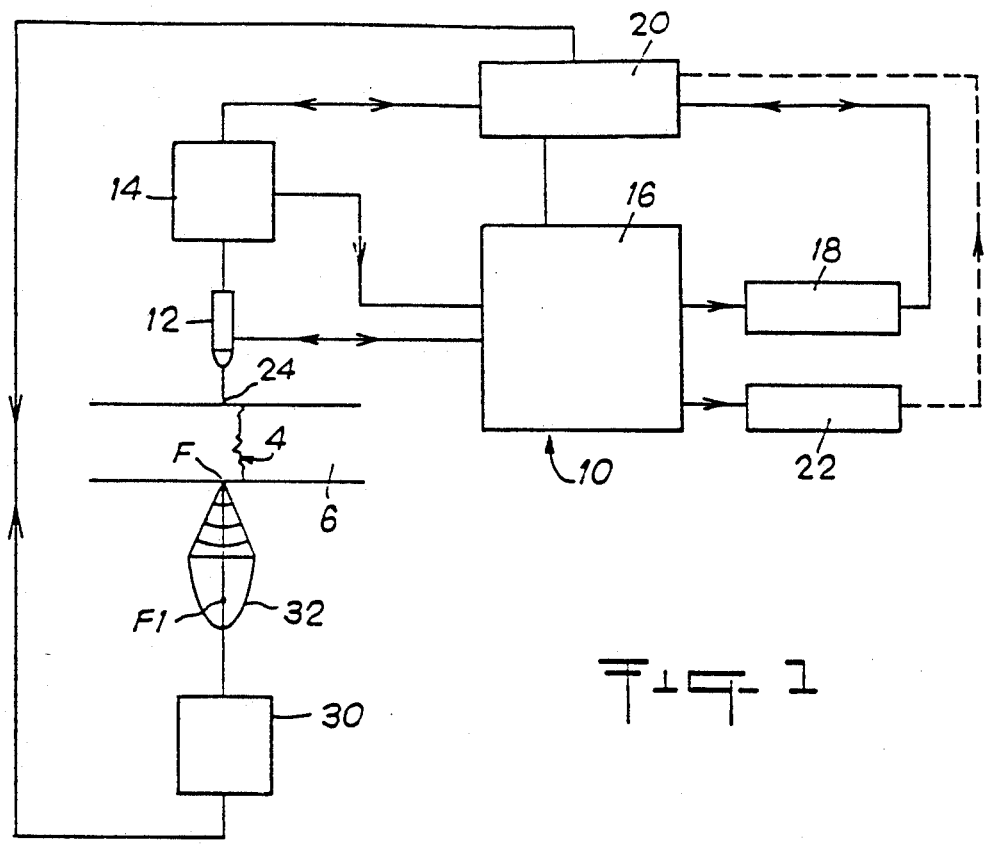
Fig-1
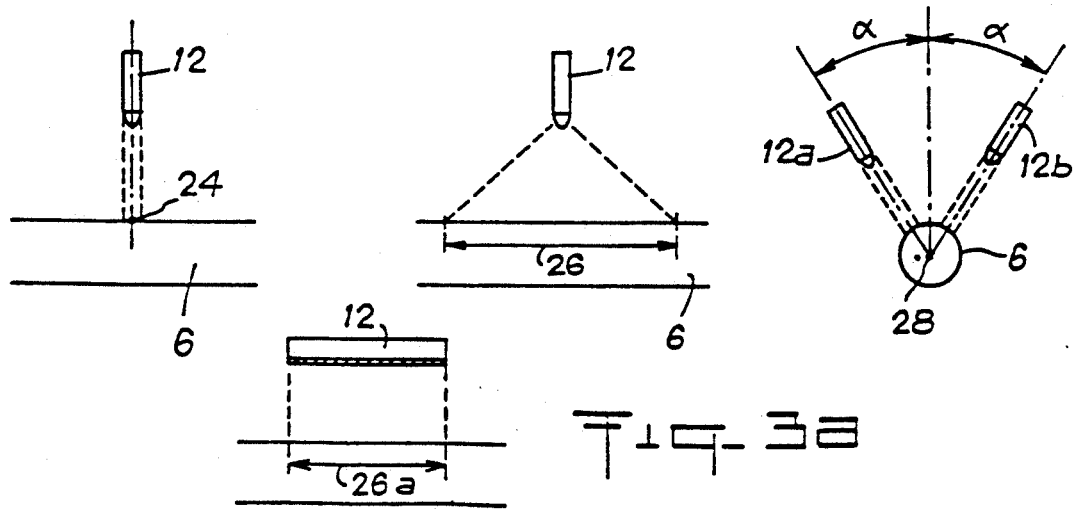
Fig-2  Fig-3  Fig-4
Fig-3a

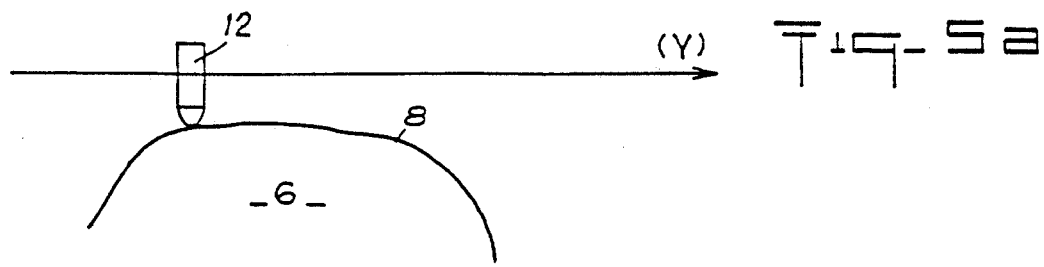
Fig-5a
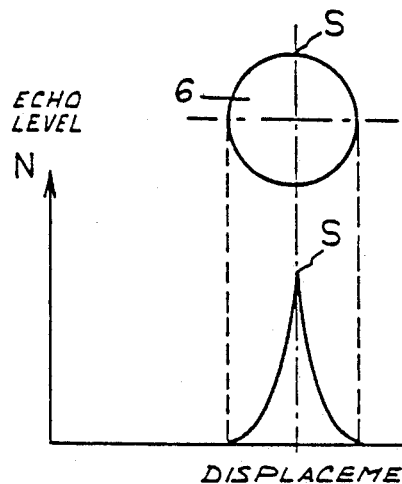
Fig-5b
Fig-5c
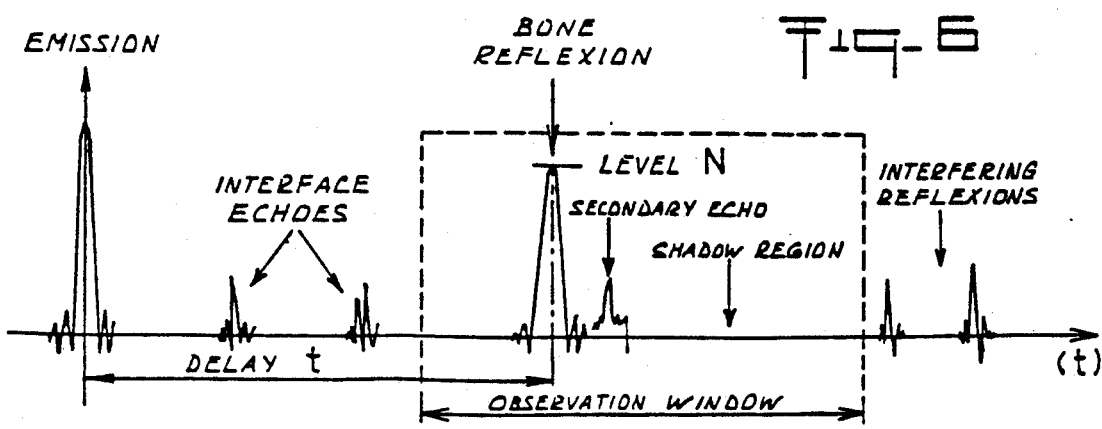
Fig-6

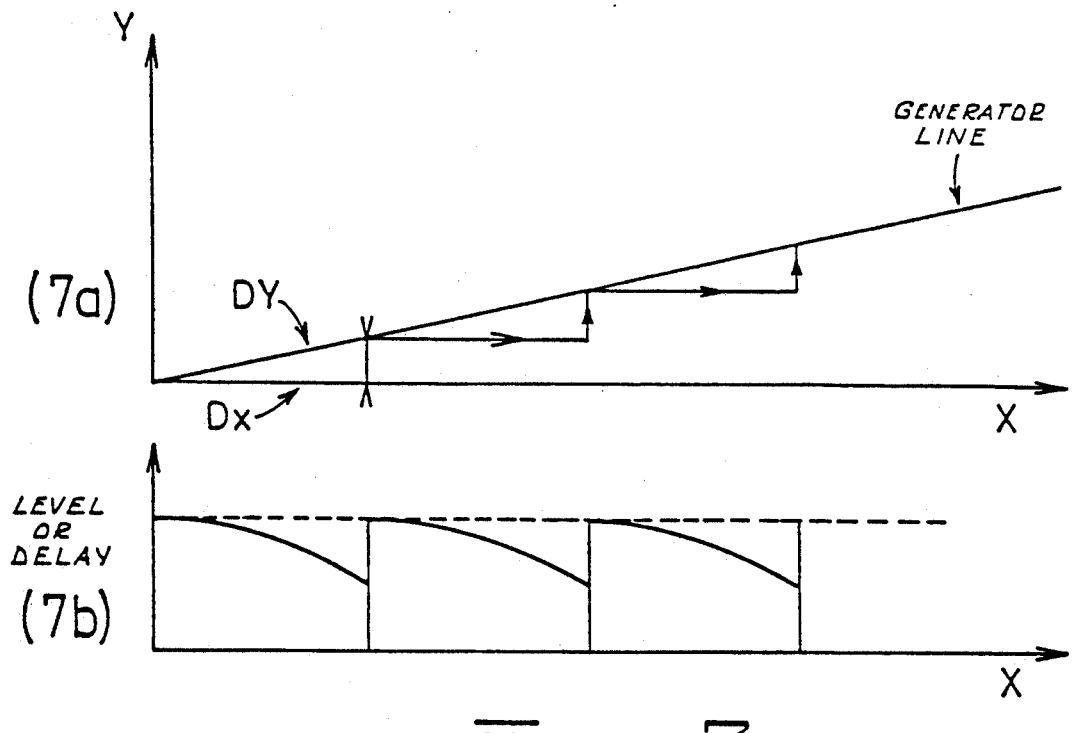
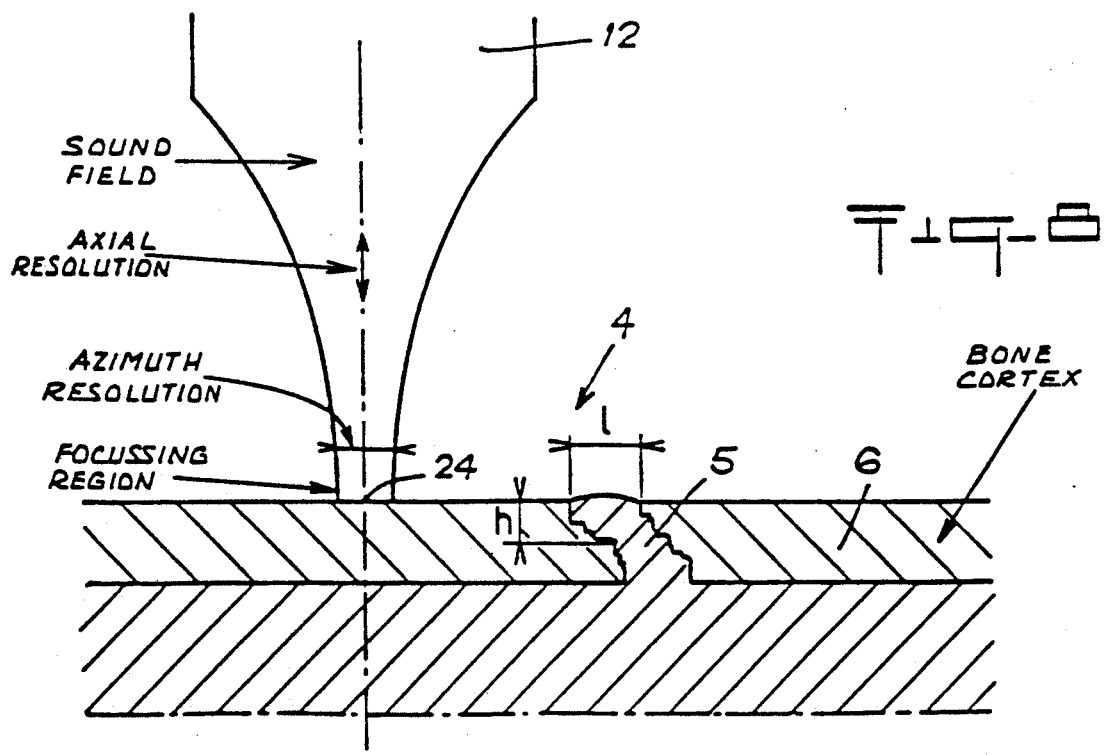

USE OF ULTRASOUND FOR DETECTING AND LOCATING A BONY REGION, METHOD AND APPARATUS FOR DETECTING AND LOCATING SUCH A BONY REGION BY ULTRASOUND

The present invention relates essentially to the use of ultrasound for detecting and locating a bony region, and also to a method and to apparatus for detecting and locating a bony region by ultrasound. More particularly, the invention uses ultrasound to detect and locate a fracture, and in a preferred application, such location and detection of a fracture is made use of in shockwave therapy for fractures.

BACKGROUND OF THE INVENTION

Document WO88/09190 describes a method and apparatus for medical treatment of the pathological state of bones by using shock waves. In practice, the apparatus comprises a lithotriptor comprising a shockwave generator device using a truncated ellipsoidal reflector, with the shock waves being generated at an internal first focus of the truncated ellipsoid and being focused on the external second focus which is caused to coincide with the target to be treated. Detection and location are performed by means of an X-ray generator disposed in an extremely accurate manner relative to the generator. Other similar documents include EP-A-0 324 163 and EP-A-0 324 711 which describe the use of a lithotriptor for fracture treatment, in particular for inducing bone growth.

However, the methods and apparatuses described in the prior art for treatment of bone pathology do not really describe the method of automatically detecting and locating the bony region to be treated. In addition, the technique generally used is the X-ray technique which suffers from the drawback of subjecting the patient to undesirable doses of X-ray irradiation that may have side effects. Radiation dosage may be important insofar as several detection and location tests are necessary during shockwave therapy.

An object of the present invention is thus to solve the novel technical problem consisting in providing a solution enabling detection and location of a bony region to be performed innocuously, i.e. without using X-rays or similar harmful radiation.

Another object of the invention is to solve the novel technical problem mentioned above by implementing a solution for automatically detecting and locating the bony region to be treated, thereby advantageously making this method and apparatus simple to apply in shockwave therapy.

The present invention solves these novel technical problems for the first time in a manner which is particularly simple and which is usable on an industrial scale.

SUMMARY OF THE INVENTION

Thus, in a first aspect, the present invention provides the use of ultrasound for detecting and locating a predetermined bony region, in particular a fracture, or bone disease such as pseudarthrosis.

In a second aspect, the present invention also provides a method of detecting and locating a determined bony region, in particular a fracture, or bone disease such as pseudarthrosis, the improvement comprising providing at least one ultrasound transducer component and using said transducer component for detecting and locating said determined bony region.

In a particular variant implementation of the method of the invention, the method comprises:

a) providing at least one ultrasound transducer component selected from a range of ultrasound frequencies enabling detected echoes to have sufficient resolution for determining the presence of said bony regions;

b) displacing the transducer component and/or a component supporting a bone including said bony region relative to each other in such a manner as to cause the transducer component to pass over said bony region;

c) causing said transducer component to emit ultrasound signals during said displacement;

d) detecting the reflected echoes of the emitted signals and comparing them with a reference echo until a change in echo level is obtained constituting a sign representative of the presence of a determined bony region, e.g. a reduction in echo level, or lateness in echo appearance, or the appearance of a secondary echo; and e) storing the position of said bony region.

In another variant specific implementation of the method of the invention, the method comprises:

a) providing at least one ultrasound transducer component, preferably mounted for displacement in three dimensions along directions X, Y, and Z, said transducer elements being selected from a range of ultrasound frequencies enabling detected echoes to have sufficient resolution for determining the presence of said bony regions;

b) displacing said transducer component relative to a component supporting the bone including said bony region, the displacement being in a direction substantially perpendicular to the longitudinal direction of the bone to be observed;

c) causing said transducer component to emit ultrasound signals during said displacement, and analyzing the level and/or the delay to the resulting echoes appearing;

d) looking for the maximum amplitude in said analysis and/or for the minimum echo appearance delay over the bony region of interest in order to generate a generator line of the bone;

e) then displacing said transducer component or said support component perpendicularly to the initial direction to follow said bone generator line as determined in this way while continuing to cause said transducer component to emit ultrasound signals;

f) detecting the echoes reflected by the emitted signals and comparing them with the reference echo until a change in the echo is detected constituting a sign that said determined bony region is present, e.g. a reduction in echo level, or lateness in echo appearance, or the appearance of a secondary echo; and g) storing the position of said bony region.

In a preferred variant implementation, the ultrasound transducer component is displaced stepwise.

In another advantageous implementation of the method of the invention, the distance between the transducer component and the surface of the bone is determined on the basis of the difference between the time at which the signal is emitted and the time at which its echo appears.

Advantageously, the stored three dimensional coordinates of said bony region are recorded in the form of coordinates for a target point that is to be put into coincidence with the focal point of a shock wave generator. Advantageously, the recorded coordinates are those of the point on the surface closest to the transducer component.

A plurality of ultrasound transducer components may be used, in particular distributed in two groups of transducer components disposed at a predetermined known angle, and the transducer components may then be displaced together until identical values are obtained for the delay to the appearance of the echo from the bone, thus enabling the bone to be placed in the midplane defined by the two groups of transducer components.

Advantageously the transducer component used is a monocrystal or a sector scanning or a "strip" type ultrasound transducer.

The ultrasound transducer component may emit ultrasound in the frequency range 3 MHz to 10 MHz, and ideally in the range 5 MHz to 7 MHz.

In a third aspect, the present invention also provides apparatus for detecting and locating a determined bony region, in particular a fracture, or bone disease such as pseudarthrosis, the apparatus comprising:

a) at least one ultrasound transducer component selected to operate in an ultrasound frequency range enabling detected echoes to have sufficient resolution for determining the presence of said determined bony region;

b) displacing means for displacing said transducer component and/or a support component for the bone including said bony region, in such a manner as to cause said transducer component to pass over said bony region;

c) emitting means for causing said transducer components to emit ultrasound signals during said displacement and detecting means for detecting the echoes emitted by reflection;

d) processor means for processing the detected signals and capable of comparing them with detected signals that serve as references, and for determining a change in the echo constituting a sign that said bony region is present, e.g. a reduction in echo level, or lateness in echo appearance, or the appearance of a secondary echo; and e) calculating and storing means for calculating and storing the position of said bony region on the basis of the changes in the echo detected by the processor means.

In a particular variant embodiment, the invention provides apparatus for detecting and locating a determined bony region, in particular a fracture or bony disease such as pseudarthrosis, characterized in that the apparatus comprises:

a) at least one ultrasound transducer component selected to operate in an ultrasound frequency range enabling the detected echoes to have sufficient resolution for determining the presence of said determined bony region;

b) displacing means for displacing said transducer component and/or a component supporting the bone including said bony region in three dimensions along directions X, Y, and Z, in such a manner as to cause said transducer component to pass over said bony region;

c) emitting means for causing the transducer component to emit ultrasound signals and detecting means for detecting echoes emitted by reflection;

d) processor means for processing the detected signals and capable of analyzing them to determine their level and/or the delay to their appearance to define a generator line of the bone which is then followed to locate said bony region itself;

e) control means for controlling the means for displacing the transducer component and/or said component for supporting the bone in three dimensions along directions X, Y, and Z and integrating, in particular, the data transmitted by the abovementioned processor means; and f) said processor means include means for determining the delay to the appearance of the echo between the transducer component and the surface of the bone when the processor means observe a change in the echo constituting a sign that said bony region is present, e.g. a reduction in level or lateness in its appearance, or the appearance of a secondary echo, and calculation and storage means for calculating and storing the position of said bony region on the basis of the determination of the delay in echo appearance.

Advantageously, the control means comprise a computer device controlling the speed and the direction of displacement of the ultrasound transducer element and/or of the bone support element, preferably as a function of initially programmed data, and also on the basis of echo data picked up by the transducer component.

Advantageously, the computer device calculates the distance between the position of the transducer component in three dimensions and the surface of the bone on the basis of the delay to echo appearance, and constitutes the above-mentioned means for calculating and storing the position of the bony region. Advantageously, the coordinates recorded are those of the point of the surface closest to the transducer component.

In another advantageous embodiment of the apparatus, it comprises a plurality of ultrasound transducer components, in particular distributed in at least two groups of transducer components disposed at a predetermined known angle, and operating simultaneously in emission and reception, thereby enabling the bone to be positioned in a midplane defined by the two groups of transducer components.

The coordinates in three dimensions of the point of said bony region which is closest to the transducer component may be transmitted by the control means as the coordinates of a target point which is to be brought into coincidence with the focal point of a shock wave generator, the control means preferably controlling displacement of a shock wave generator in three dimensions so that its focal point coincides with the target point.

The characteristics of the ultrasound transducer component are as described above in the context of the method.

For example, a microcrystal transducer may be used which is focused by an acoustic lens, or a transducer of the fixed focal length "cup" type; or a transducer of the variable focal length "annular" type. It is also possible to use sector scanning ultrasound transducers, or fixed focal length strip type transducers, or "phased array" type transducers.

The use of sector scanning or "strip" type ultrasound transducers is advantageous in that it makes it possible to avoid displacing the transducer components during the stage of detecting the looked-for bony region, or optionally to construct an echographic image without displacing the transducer.

Advantageously, the detection and location apparatus comprises a plurality of transducer components. Preferably, these transducer components are distributed in at least two groups of transducer components disposed at a known angle to each other and operating simultaneously in transmission and in reception, thereby enabling the bone to be positioned in a midplane defined by the two groups of transducer components.

Advantageously, the set of transducer components is mounted on a moving system whose movements in three dimensions are encoded relative to a fixed reference. The fixed reference may be constituted by a component fixed to the device supporting the patient and easily detectable by ultrasound, e.g. having a special geometrical shape.

It is also possible to cause the transducer components to be fixed in position and to place the bone, and thus the patient, on a moving device.

It is also possible by using transducer components having a focus line to provide the transducer components and the patient support means mounted on systems that remain fixed even though such systems do not provide maximum freedom to the practitioner.

By using ultrasound transducer components, i.e. echo-graphic means, the invention makes it possible to escape from constraints related to radiation, in particular X-ray radiation, and to obtain information rapidly suitable for use by simple computer and electronic means, thereby making it possible to control the shockwave generator apparatus in real time without requiring complex image processing, thus making it possible to automate the therapeutic process, and to reduce the time required for treatment considerably.

Thus, in a fourth aspect, the present invention also provides apparatus for generating shock waves focused on a focal point to be brought into coincidence with a target point, the apparatus comprising control means controlling displacement of a shock wave generator in three dimensions so that its focal point coincides with said target point, wherein the control means determine the coordinates of the target point as being the coordinates of a point of a determined bony region to be treated, said coordinates of the point of said bony region being obtained by using at least one ultrasound transducer element, in particular by implementing the above-mentioned method or apparatus for detecting and locating a bony region.

In a variant embodiment, the shockwave generator apparatus includes a shock wave generator selected from the group comprising: a truncated ellipsoidal reflector filled with a liquid such as water and optionally closed by a membrane; a focused hemispherical cup component; and focused magnetostrictive components.

In another variant embodiment, the transducer component is integrated in or is mechanically connected to the focused shock wave generator such that they are displaced simultaneously.

BRIEF DESCRIPTION OF THE DRAWINGS

Preferred embodiments of the invention are described by way of example with reference to the accompanying drawings, in which:

FIG. 1 is a diagrammatic block diagram of apparatus for detecting and locating a determined bony region, in particular a fracture or bone disease such as pseudarthrosis, and applied in a preferred implementation to apparatus for generating shock waves;

FIG. 2 shows a variant embodiment of the detection apparatus of the invention constituted by a monocrystal ultrasound transducer component;

FIG. 3 shows a variant embodiment of the detection apparatus constituted by a sector-scanning ultrasound transducer component;

FIG. 3a shows a variant embodiment of the detection apparatus constituted by a "strip" type transducer;

FIG. 4 shows a variant embodiment of the detection apparatus constituted by transducer components distributed over at least two groups of transducer components disposed at a predetermined angle relative to the vertical;

FIG. 5 shows at 5a one example of displacing the transducer component along the Y axis relative to a bone, at 5b it shows the level of the resulting echo as a function of displacement in the Y direction, and FIG. 5c shows the time delay of echo appearance as a function of displacement in the Y direction;

FIG. 6 shows curves of ultrasound transmission, interface echo, bone reflection, and interfering reflection, together with the observation window that covers the maximum echo level;

FIG. 7 shows at 7a stepwise displacement of the ultrasound component in the X and Y directions, and at 7b it shows the corresponding reflected sound echo;

FIG. 8 is a diagram of the acoustic field of an ultrasound transducer component with its focusing zone and in the vicinity of a determined bony region, e.g., in this case, a fracture.

DETAILED DESCRIPTION

Figure 9:
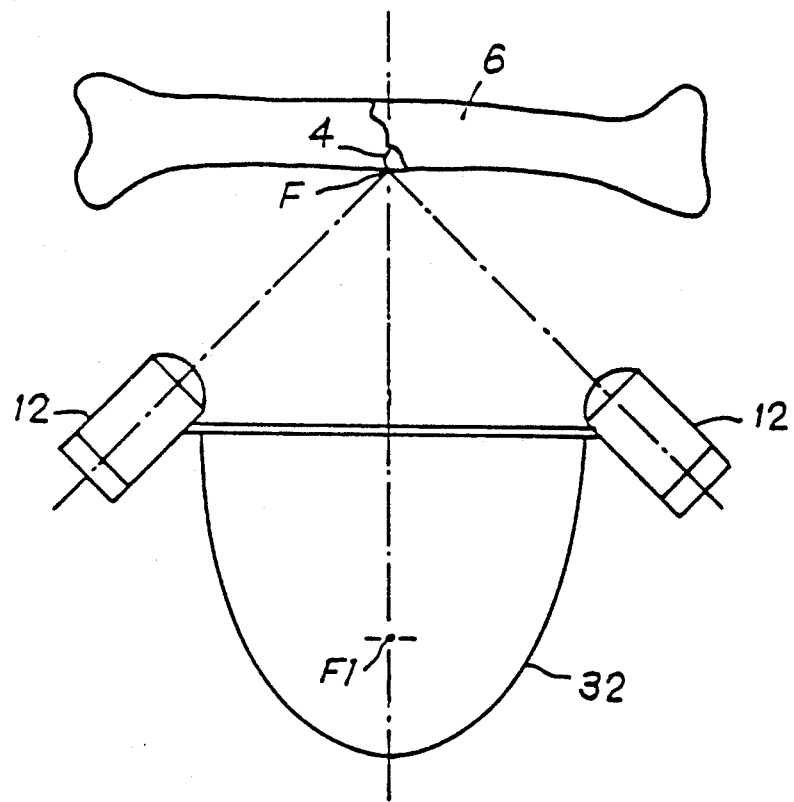
FIG. 9 shows a preferred embodiment in which the transducer component is integrated in or mechanically bonded to the generator of focused shock waves, such that their displacements take place simultaneously.

With reference to the figures, and in particular to FIG. 1, apparatus for detecting and locating a bony region 4 on a bone 6 of a patient is given general reference numeral 10. This apparatus is characterized in that it comprises at least one ultrasound transducer component 12. The ultrasound transducer component 12 is selected from a range of ultrasound frequencies that enable detected echoes to be obtained that have sufficient resolution for determining the presence of the bony region 4.

In an advantageous variant embodiment of the apparatus of the invention, the apparatus is characterized in that it includes means 14 for displacing the transducer component 12 in three dimensions X, Y, and Z. These displacement means include means for encoding in Cartesian coordinates X, Y, and Z and/or in polar coordinates R, theta, phi.

This apparatus also includes means 16 for emitting signals to the transducer component 12 and means for detecting echoes provided by reflection, and integrated in an electronic device which is well known to the person skilled in the art. The apparatus of the invention also or advantageously includes processor means 18 for processing the detected signals and capable of comparing them with detected signals that serve as a reference, said processor means including means for determining the distance between the transducer component and the surface of the bone on the basis of the time delay before the echo reflected by the bone appears, with such determination taking place whenever the processor means observes a change in the echo constituting a sign that the bony region 4 is present, e.g. a reduction level or lateness in echo appearance, or indeed the appearance of a secondary echo.

The apparatus of the invention also advantageously includes means 20 for controlling the means 14 for displacing the transducer element 12 in three dimensions X, Y, and Z, and integrating in particular the data transmitted by the processor means 18, e.g. by having a computer device present therein.

In a variant embodiment, an imaging device 22 could optionally be provided for constituting an image of the focus region on the basis of data collected by the means 16.

In a preferred application of the detection and location apparatus of the invention, the transducer component 12 is integrated in or mechanically linked to apparatus 30 for generating shock waves focused on a focal point F, and in particular to a focused generator device 32, e.g. a truncated ellipsoid 32 emitting shock waves at an internal focus F1, which waves are focused at the external focus F, as is well known to the person skilled in the art, and as is shown in FIG. 9.

According to the invention, the means 20 for controlling the means 14 for displacing the transducer component 12, e.g. including a computer device, also control three-dimensional displacement in directions X, Y, and Z of the shock wave generator 32 which also includes encoding means operating in Cartesian coordinates X, Y, and Z and/or in polar coordinates, R, theta, and phi. In this way, the control means 20 including a computer device are common to the apparatus for detecting and locating a bony region and to the shock wave generator apparatus, and this constitutes an important advantage of the invention.

It should be observed that the position coordinates in three dimensions of the ultrasonic transducer component 12 and of the shock wave generator 32 are encoded relative to a fixed reference. This fixed reference may be constituted, for example, by a component which is fixed to the device supporting the patient and which is easily detected by ultrasound, e.g. a component having a special geometrical shape.

As mentioned above, the transducer component 12 may be a monocrystal (focus point 24) as shown in FIG. 2, or it may be a sector scanning component (focus line 26) as shown in FIG. 3, or it may be of the "strip" type (focus line 26a) as shown in FIG. 3a. In addition, in another variant embodiment, a plurality of transducer components may be provided in at least two groups 12a and 12b which are disposed relative to each other at an angle α relative to the vertical such that the ultrasound beams emitted intersect at intersection point 28 which may lie inside or on the surface of the bone 6. This intersection point 28 is also situated vertically relative thereto, as can clearly be seen in FIG. 4.

In FIG. 5, FIG. 5a represents the displacement of an ultrasound transducer component 12 along the Y axis over the surface of the skin 8 of a limb of a patient containing a bone 6 to be observed. FIG. 5b is a graph with the level N of the reflected echo being plotted vertically as a function of displacement along the horizontal Y-axis, with the position S closest to the bone corresponding to the maximum reflected echo. FIG. 5c shows the delay to echo appearance as a function of displacement along the horizontal Y axis, and it can be seen that the closest point S corresponds to the shortest delay before the echo appears.

FIG. 6 shows the sound level of the emitted signal and of the interface, bone reflection, and interfering echoes as a function of time, and this figure also shows an observation window which is the time interval that is observed for detecting the echo from reflection on the bone 4.

FIG. 7 shows stepwise displacement of the ultrasound component 12 by the displacement means 14 under control of the control means 20 through a distance Dx along the X-axis and through a distance DY along the Y-axis (FIG. 7a). FIG. 7b shows the level or the delay of the reflected sound echo during the above displacements Dx and DY.

FIG. 8 is a fragmentary view on an enlarged scale showing the looked-for bony region 4, e.g. constituted by a fracture 5 defining a break in the bone 6 occupying a width 1 and a depth equal to h, for example, and also showing the focus zone, e.g. 24, of the transducer component 12. It may be observed that it is advantageous for the focus zone 24 to provide sufficient resolution to detect the fracture 4, and, in this case, for it to be smaller than the width 1 of the break caused by the fracture 5, for example.

It will be understood that the apparatus described above can be used for performing the method of detecting and locating a determined bony region as described above. In practice, a preferred implementation of the method takes place as follows:

a) Detecting bone

The transducer component 12 is displaced automatically by means of its support means 14 in a direction which is substantially perpendicular to the longitudinal direction of a bone 6 to be observed. The position in three dimensions of the transducer element 12, i.e., in practice, the position of its support means 14, is transmitted to the means 16 and to the processor means 18. Simultaneously with this displacement, the means 16 cause electrical signals to be sent to the transducer components 12 and receive electric signals emitted by the ultrasound transducer components 12 as a result of reflected echoes, and in particular echoes reflected within the observation time window which includes the maximum level of the echo, and suitable for determining the delay before it appears.

When the transducer element comes vertically over the generator line of the bone S closest to the ultrasound transducer 12 (see FIG. 5a), the level of the reflected echo is at a maximum (FIG. 5b) and the delay to appearance of the echo is at a minimum (FIG. 5c). These two conditions thus make it possible to determine the presence of and the position of the bone 6. It is advantageous to make use of these two concordant sources of information to verify each against the other.

As shown in FIG. 4, in another variant of the method of the invention for detecting a bone, at least two groups of transducer components are used which are at a known angle (2α) to each other. These two groups of transducer components 12a and 12b operate simultaneously in emission and in reception. For each group, the delay to bone echo appearance during a movement similar to that described above for a single group of transducer components is determined. When both appearance delays have the same value, then the bone is situated in the midplane defined by the two groups of transducer components 12a and 12b. This variant of the method of the invention serves simultaneously to detect the bone 6 and to determine its position relative to the detector apparatus defined by the transducer components 12 mounted on the support means 14.

The means 16 and the means 18 provide electronic processing of the electrical signals transmitted by the transducer components 12 to determine the maximum levels and the minimum delays of reflected echoes appearing, and this information is transmitted to the control means 20 which generally comprise a computer device which in turn controls the displacement in three dimensions of the support means 14 and thus of the transducer components 12. Once the position of the bone has been detected, the next stage consists in following a generator line of the bone.

b) Following a bone generator line

Once the generator line of the bone has been detected along the longitudinal direction of the bone, the transducer component 12 is displaced along said generator line by displacing its support means 14 under control of the control means 20, which generator line, may, for example, be parallel to or coincide with the X-axis. Thus, after displacing the transducer component 12 along the Y-axis perpendicular to the longitudinal axis of the bone (i.e. the X-axis), the transducer component 12 is then displaced parallel to the longitudinal direction of the bone, i.e. along the X-axis. If displacement along the X-axis does not coincide exactly with the longitudinal direction of the bone, then the transducer component 12 moves away from the generator line and the level of the echo diminishes. The generator line of the bone is then found again by scanning in identical manner to the preceding stage to find a maximum in the signal for a perpendicular displacement along the Y-axis. The generator line of the bone is thus followed by looking for the maximum echo level on displacement in the Y direction (DY) (FIG. 7) after each displacement along the X-axis (Dx).

In the variant embodiment using at least two groups of transducer components 12a and 12b, the generator line of a bone is followed by a looking for the displacement DY at each step Dx that enables the same delay in the appearance of the bone echo to be obtained in each of the groups of transducer components 12a and 12b. Under these conditions, the bone is recentered in the midplane defined by the two groups of transducer elements 12a and 12b. The same means 16, 18, and 20 are used to perform the detection stage and the stage of following the generator line of the bone.

While following the generator line of the bone, the looked-for bony region is detected and located.

c) Detecting the looked-for region

The looked-for bony region is detected and located on the basis of a discontinuity in the bone medium in the region of interest 4, thereby causing a transient disturbance in the echographic signal.

As will readily be understood from looking at FIG. 8, this disturbance gives rise to the echo appearing late by a time t which is related to the size h of the bony discontinuity due, for example, to a fracture 5, and also to the reduction in echo level L due to various reflections and transmissions in the cortex of the bone 6, or to the appearance of a secondary echo.

Optimization of the axial resolution and the azimuth resolution characteristic gives rise to the best adapted transducers being selected.

Thus, and as in the above context of detecting the bone and following its generator line, the means 16, 18, and 20 enable discontinuities in electrical signals to be detected. The invention naturally makes it possible to analyze the signal from a single transducer 12 or from a plurality of transducer components when looking for discontinuities in bone.

It will also be understood that the information concerning echo level and delay before echo appearance can also be made use of simultaneously to provide a check on the presence of the bone discontinuity, e.g. a fracture 5, by using two independent criteria. The bone discontinuity may also be constituted by arthrosis or by pseudarthrosis.

Once the looked-for bony region has been detected, it is then located as follows.

d) Locating a bone discontinuity in three dimensions

Once a bone discontinuity has been detected as described above, information concerning the position of the transducer component 12 and the delay to an echo appearing from the bone as obtained by the processor means 18 is transmitted to the control means 20 which includes the computer device where said information is stored in a memory. The data is then processed computationally to deduce the position in three dimensions of the looked-for bony region.

In the context of the preferred application to apparatus for generating shock waves 30, the control means 20 control displacement of the shock wave generator 32 in such a manner that its target focus F is disposed appropriately relative to the bony region 4 for performing shock wave treatment. The shock wave treatment may be performed as described in the above-mentioned document. However, the apparatus of the invention may be implemented in associated with any kind of shock wave generator since the shock wave generator is completely independent of the technology chosen for the apparatus of the invention.

However, an important advantage of the present invention lies in the fact that the control means 20 include a computer device which controls the entire system used, and in particular which also controls the shock wave generator both with respect to generator positioning and with respect to firing the shock waves themselves, thereby making it possible to automate the therapy process and considerably reduce the duration of treatment. By using the method and apparatus of the invention, it is possible to perform treatment of pseudarthrosis without requiring open surgery, and to accelerate the consolidation of limb fractures, or of other bones without requiring open surgery. It is also possible to perform prosthesis release or elimination or prosthesis cement. Thus, the looked-for bony region may either be a fracture, or a region of arthrosis or of pseudarthrosis, or a prosthesis, or prosthesis cement, thereby increasing the universality of the method and apparatus of the invention.

In order to obtain effective resolution, it is preferable to use ultrasound transducer components that emit in the frequency range 3 MHz to 10 MHz, and ideally in the range 5 MHz to 7 MHz.

Naturally, the invention extends to all technical means that constitute technical equivalents of the means described, and to various combinations thereof. For example, the support means 14 supporting the transducer components 12 may be fixed to the shock wave generator thus constituting a single moving assembly. In another variant embodiment, it is possible to make use of the echographic images produced by the imaging means 22 as built up by the electronic device 16. Thus, by electronic processing of the video signal, it is possible to look for the bony region of interest directly in the image and to calculate its position in three dimensions. This information is then transmitted by the control means 20 which include a computer device to the shock wave generator 32 in a manner similar to that described above.

The invention is applicable to any apparatus for generating shock waves. In particular, it may be applied to a shock wave generator selected from the group consisting in a truncated ellipsoidal reflector filled with a liquid such as water, optionally closed by membrane, a hemispherical focused cup component, and focused magnetostrictive components.

We claim:

1. A method of detecting and locating a predetermined bony region in a bone, including at least one of a fracture and a bone disease, the method comprising the steps of:
   a) providing at least one ultrasound transducer component, mounted for displacement in three dimensions along directions X, Y, and Z, said at least one ultrasound transducer component being selected to operate in a range of ultrasound frequencies enabling detected echoes to have sufficient resolution for determining the presence of said predetermined bony region;
   b) displacing said at least one ultrasound transducer component relative to a component supporting the bone including the predetermined bony region, the displacement being in an initial direction substantially perpendicular to the longitudinal direction of the bone to be observed;
   c) causing said at least one ultrasound transducer component to emit ultrasound signals during said displacement, and analyzing at least one of the amplitudes of echoes reflected from said emitted ultrasound signals and the delay of the echoes;
   d) locating at least one of a maximum of the amplitude of the echoes and a minimum of the delay of said echoes for generating a generator line of the bone;
   e) then displacing one of said at least one ultrasound transducer component and said support component perpendicularly to said initial direction to follow said bone generator line as generated in said locating step while said transducer component emits ultrasound signals;
   f) detecting the echoes from the signals emitted in step (e) and comparing them with a reference echo until a change in the echo is detected constituting an indication that said predetermined bony region is present, said indication comprising one of a reduction in echo level, lateness in echo appearance, and the appearance of a secondary echo; and
   g) storing the position of said bony region.

2. The method of claim 1, wherein said at least one ultrasound transducer component is displaced in said displacing step in a stepwise manner.

3. The method of claim 1, wherein the distance between said at least one ultrasound transducer component and the surface of the bone is determined on the basis of the difference between the time at which the ultrasound signal is emitted and the time at which its echo appears.

4. The method of claim 1, wherein the stored position of said bony region is recorded as three dimensional coordinates for a target point that is placed into coincidence with the focal point of a shock wave generator, with the recorded coordinates comprising the point on the surface closest to said at least one transducer component.

5. The method of claim 1, wherein a plurality of ultrasound transducer components are arranged in two groups of transducer components disposed at a predetermined angle, and wherein the transducer components are displaced simultaneously until identical values are obtained for the delay to the appearance of the echo from the bone, thereby the bone is placed in the midplane defined by the two groups of transducer components.

6. The method of claim 1, wherein said at least one ultrasound transducer component comprises a transducer selected from the group consisting of a monocrystal, a sector scanning, and a "strip" type ultrasound transducer.

7. The method of claim 1, wherein said at least one ultrasound transducer component emits ultrasound in the frequency range 3 MHz to 10 MHz.

8. The method of claim 7, wherein said at least one ultrasound transducer component emits ultrasound in the frequency range 5 MHz to 7 MHz.

9. Apparatus for detecting, locating, and treating a predetermined bony region in a bone, including at least one of a fracture and a bone disease, the apparatus comprising:
   a) at least one ultrasound transducer component selected to operate in an ultrasound frequency range enabling detected echoes to have sufficient resolution for determining the presence of the predetermined bony region;
   b) displacing means for displacing at least one of said at least one ultrasound transducer component and a support component for the bone including the predetermined bony region, for causing said at least one ultrasound transducer component to pass over the predetermined bony region;
   c) emitting means for causing said at least one ultrasound transducer component to emit ultrasound signals during said displacement and detecting means for detecting the reflected echoes;
   d) processor means for processing the detected echoes and comparing them with reference echoes, and for determining a change in the echo constituting an indication that said bony region is present, said change in the echo comprising at least one of a reduction in echo level, lateness in echo appearance, and the appearance of a secondary echo;
   e) calculating and storing means for calculating and storing the position of said bony region on the basis of the changes in the echo detected by said processor means;
   f) a shock wave generator having a focal point (F) to be brought into coincidence with a target point in the predetermined bony region; and
   g) means for controlling displacement of said generator for moving the focal point into coincidence with the target point, the position of said target point corresponding to a position on the predetermined bony region to be treated.

10. The apparatus of claim 9, comprising a plurality of ultrasound transducer components arranged in at least two groups of transducer components disposed at a predetermined angle, and operating simultaneously with said emitting means, thereby the bone is positioned in a midplane defined by the two groups of transducer components.

11. The apparatus according to claim 9, wherein said shock wave generator is selected from the group consisting of an ellipsoidal reflector filled with a liquid such as water and optionally closed by a membrane, a focused hemispherical cup component, and a focused magnetostrictive component.

12. The apparatus of claim 9, wherein said ultrasound transducer component is connected to the shock wave generator for displacement therewith.

13. Apparatus for detecting and locating a predetermined bony region in a bone disposed on a component support and including at least one of a fracture and bone disease, said apparatus comprising:
   a) at least one ultrasound transducer component selected to operate in an ultrasound frequency range enabling detected echoes to have sufficient resolution for determining the presence of said predetermined bony region;
   b) displacing means for displacing at least one of said at least one ultrasound transducer component and the component support in three dimensions along directions X, Y, and Z, for causing said at least one ultrasound transducer component to pass over the predetermined bony region;
   c) emitting means for causing said at least one ultrasound transducer component to emit ultrasound signals and detecting means for detecting the reflected echoes;
   d) processor means for processing the detected echoes and analyzing them to determine at least one of their level and the delay to their appearance for defining a generator line of the bone which is then followed to locate the predetermined bony region;
   e) control means for controlling the means for displacing at least one of said at least one ultrasonic transducer component and said component support for relative movement substantially along said generator line and integrating the data transmitted by said processor means;
   f) said processor means including means for determining the delay to the appearance of the echo between said at least one ultrasound transducer component and the surface of the bone when said processor means observe a change in the echo constituting an indication that said bony region is present, said echo change comprising at least one of a reduction in level, lateness in echo appearance, and the appearance of a secondary echo; and
   g) calculation and storage means for calculating and storing the position of the predetermined bony region on the basis of the determination of the delay in echo appearance when said processor means observe said change in echo.

14. The apparatus of claim 13, wherein said control means comprise a computer device controlling the speed and the direction of displacement of at least one of said at least one ultrasound transducer component and the component support as a function of initially programmed data and on the basis of the echoes detected by said detecting means for defining said generator line.

15. The apparatus of claim 14, wherein said computer device (a) calculates the distance between the position of said at least one ultrasound transducer component in three dimensions and the surface of the bone on the basis of the echoes detected by said detecting means, and (b) calculates and stores the position of the predetermined bony region.

16. The apparatus of claim 13, wherein the coordinates in three dimensions of the point of the predetermined bony region which is closest to said at least one ultrasound transducer component are transmitted by said control means as the coordinates of a target point which is to be brought into coincidence with the focal point of a shock wave generator, said control means controlling displacement of a shock wave generator in three dimensions so that its focal point (F) coincides with the target point.

* * * * *